United States Patent
Dimov et al.

(10) Patent No.: US 11,080,848 B2
(45) Date of Patent: Aug. 3, 2021

(54) IMAGE-BASED DISEASE DIAGNOSTICS USING A MOBILE DEVICE

(71) Applicant: Lucira Health, Inc., Emeryville, CA (US)

(72) Inventors: Ivan Krastev Dimov, Union City, CA (US); Frank B. Myers, III, Richmond, CA (US); John Robert Waldeisen, Berkeley, CA (US); Debkishore Mitra, Berkeley, CA (US)

(73) Assignee: Lucira Health, Inc., Emeryville, CA (US)

( * ) Notice: Subject to any disclaimer, the term of this patent is extended or adjusted under 35 U.S.C. 154(b) by 333 days.

(21) Appl. No.: 16/155,829

(22) Filed: Oct. 9, 2018

(65) Prior Publication Data

US 2019/0050988 A1    Feb. 14, 2019

Related U.S. Application Data

(63) Continuation-in-part of application No. 15/481,349, filed on Apr. 6, 2017, now Pat. No. 10,146,909.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0059* (2013.01); *A61B 5/1032* (2013.01);
(Continued)

(58) Field of Classification Search
CPC ........ G01N 33/50; G01N 21/76; G01N 21/75; G01N 21/78; G01N 21/6428;
(Continued)

(56) References Cited

U.S. PATENT DOCUMENTS

| D244,555 S | 5/1977 | Wiedmann |
| 4,310,488 A | 1/1982 | Rahm et al. |

(Continued)

FOREIGN PATENT DOCUMENTS

| AU | 2003272465 A1 | 4/2004 |
| CA | 2495252 A1 | 3/2004 |

(Continued)

OTHER PUBLICATIONS

Anonymous: "Image Enhancement and Verification Tools—ABBYY Mobile Imaging SDK," Jul. 13, 2014, 12 pages.

(Continued)

*Primary Examiner* — Shogo Sasaki
(74) *Attorney, Agent, or Firm* — Goodwin Procter LLP (57) ABSTRACT

A diagnostic system performs disease diagnostic tests using at least an optical property modifying device and a mobile device. A user provides a biological sample from a patient to the optical property modifying device that reacts with a reagent in one or more reaction chambers of the device. The user captures one or more images of the one or more reaction chambers using an optical sensor of the mobile device. The diagnostic system can determine a quality level of the images based on factors such as skew, scale, focusing, shadowing, or white-balancing. Based on an analysis of the captured image, the diagnostic system can determine a test result of a disease diagnostic test for the patient. The diagnostic system may communicate the test result, as well as instructions for the disease diagnostic test, to the user via the mobile device.

19 Claims, 8 Drawing Sheets

(51) Int. Cl.
| | |
|---|---|
| *G06T 7/60* | (2017.01) |
| *G06T 7/90* | (2017.01) |
| *G16B 40/00* | (2019.01) |
| *A61B 5/103* | (2006.01) |
| *G16H 50/20* | (2018.01) |
| *G16H 10/40* | (2018.01) |
| *G16H 30/40* | (2018.01) |

(52) U.S. Cl.
CPC .......... *A61B 5/6898* (2013.01); *A61B 5/7282* (2013.01); *A61B 5/742* (2013.01); *G06T 7/60* (2013.01); *G06T 7/90* (2017.01); *G06T 7/97* (2017.01); *G16B 40/00* (2019.02); *G16H 10/40* (2018.01); *G16H 30/40* (2018.01); *G16H 50/20* (2018.01); *A61B 2576/00* (2013.01)

(58) Field of Classification Search
CPC .. C12Q 1/6804; C12Q 1/6906; C12Q 1/6806; A61B 5/742; A61B 5/7282; A61B 5/0059; A61B 2576/00; A61B 5/1032; A61B 5/6898; G06T 7/97; G06T 7/60; G06T 7/90; G06T 7/0012; G16B 40/00; G16H 10/40; G16H 50/20; G16H 30/40

See application file for complete search history.

(56) References Cited

U.S. PATENT DOCUMENTS

| | | |
|---|---|---|
| 4,379,848 A | 4/1983 | Yeaw |
| 4,624,929 A | 11/1986 | Ullman |
| 4,849,340 A | 7/1989 | Oberhardt |
| 4,859,610 A | 8/1989 | Maggio |
| 4,936,682 A | 6/1990 | Hoyt |
| D334,065 S | 3/1993 | Collister |
| D371,605 S | 7/1996 | Wong et al. |
| 5,580,794 A | 12/1996 | Allen |
| 5,830,714 A | 11/1998 | Swaminathan et al. |
| 5,837,546 A | 11/1998 | Allen et al. |
| 5,888,826 A | 3/1999 | Ostgaard et al. |
| 6,074,606 A | 6/2000 | Sayles |
| 6,180,395 B1 | 1/2001 | Skiffington et al. |
| 6,198,107 B1 | 3/2001 | Seville |
| 6,336,900 B1 | 1/2002 | Alleckson et al. |
| 6,352,838 B1 | 3/2002 | Krulevitch et al. |
| 6,564,968 B1 | 5/2003 | Terrell et al. |
| 6,565,808 B2 | 5/2003 | Hudak et al. |
| 6,817,256 B2 | 11/2004 | Mehra et al. |
| 6,900,059 B1 | 5/2005 | Shinn et al. |
| D507,351 S | 7/2005 | Birnboim |
| 7,156,809 B2 | 1/2007 | Quy |
| D559,996 S | 1/2008 | Okamoto et al. |
| D560,812 S | 1/2008 | Powell et al. |
| D561,905 S | 2/2008 | Ramel et al. |
| D574,507 S | 8/2008 | Muir et al. |
| 7,438,852 B2 | 10/2008 | Tung et al. |
| 7,452,667 B2 | 11/2008 | Liew et al. |
| D608,885 S | 1/2010 | Sneddon et al. |
| 7,850,922 B2 | 12/2010 | Gallagher et al. |
| D659,848 S | 5/2012 | TerMaat et al. |
| D669,375 S | 10/2012 | Kao et al. |
| D686,311 S | 7/2013 | Mori |
| D687,564 S | 8/2013 | Yang et al. |
| 8,719,989 B1 | 5/2014 | Qanaei |
| 9,034,606 B2 | 5/2015 | Tanner et al. |
| 9,074,243 B2 | 7/2015 | Tanner et al. |
| 9,074,249 B2 | 7/2015 | Tanner et al. |
| D743,571 S | 11/2015 | Jackson |
| D748,813 S | 2/2016 | Ishiguro et al. |
| D749,420 S | 2/2016 | Maggio |
| 9,278,321 B2 | 3/2016 | Dale et al. |
| D773,069 S | 11/2016 | Curry |
| 9,546,358 B2 | 1/2017 | Tanner et al. |
| D791,952 S | 7/2017 | Florescu et al. |
| 9,739,743 B2 | 8/2017 | Athanasiou et al. |
| D800,912 S | 10/2017 | Uzri et al. |
| D808,833 S | 1/2018 | Abbott et al. |
| D820,130 S | 6/2018 | Khattak et al. |
| D821,602 S | 6/2018 | Sever et al. |
| 9,999,889 B2 | 6/2018 | Khattak et al. |
| D825,772 S | 8/2018 | Sever et al. |
| 10,146,909 B2 | 12/2018 | Dimov et al. |
| D838,379 S | 1/2019 | Trump |
| 10,195,606 B2 | 2/2019 | Khattak et al. |
| 10,253,357 B2 | 4/2019 | Mitra et al. |
| 10,272,434 B2 | 4/2019 | Khattak et al. |
| D855,212 S | 7/2019 | Komuro |
| D859,683 S | 9/2019 | Harding et al. |
| D860,472 S | 9/2019 | Blake et al. |
| D865,212 S | 10/2019 | Kakuda et al. |
| D867,584 S | 11/2019 | Zercher et al. |
| D869,311 S | 12/2019 | Khattak et al. |
| 10,545,161 B2 | 1/2020 | Khattak et al. |
| 10,549,275 B2 | 2/2020 | Myers, III et al. |
| D879,319 S | 3/2020 | Kakuda et al. |
| D879,320 S | 3/2020 | Kakuda et al. |
| 10,589,267 B2 | 3/2020 | Khattak et al. |
| 10,603,664 B2 | 3/2020 | Khattak et al. |
| 2003/0123994 A1 | 7/2003 | Weng et al. |
| 2003/0157503 A1 | 8/2003 | McGarry et al. |
| 2004/0018634 A1 | 1/2004 | Hajizadeh et al. |
| 2004/0052689 A1 | 3/2004 | Yao |
| 2004/0118189 A1 | 6/2004 | Karp et al. |
| 2004/0166569 A1 | 8/2004 | Marziali et al. |
| 2004/0209275 A1 | 10/2004 | Liew et al. |
| 2005/0022895 A1 | 2/2005 | Barth et al. |
| 2005/0221281 A1 | 10/2005 | Ho |
| 2006/0078929 A1 | 4/2006 | Bickel et al. |
| 2006/0094004 A1 | 5/2006 | Nakajima et al. |
| 2006/0166354 A1 | 7/2006 | Wikswo et al. |
| 2006/0194207 A1 | 8/2006 | Mitani et al. |
| 2006/0245977 A1 | 11/2006 | Bodner |
| 2007/0166200 A1 | 7/2007 | Zhou et al. |
| 2007/0183934 A1 | 8/2007 | Diercks et al. |
| 2007/0217963 A1 | 9/2007 | Elizarov et al. |
| 2008/0000892 A1 | 1/2008 | Hirano et al. |
| 2008/0038713 A1 | 2/2008 | Gao et al. |
| 2008/0149840 A1 | 6/2008 | Handique et al. |
| 2008/0204380 A1 | 8/2008 | Shin et al. |
| 2008/0233015 A1 | 9/2008 | Turner |
| 2009/0004732 A1 | 1/2009 | LaBarre et al. |
| 2009/0048115 A1 | 2/2009 | Liew et al. |
| 2009/0071911 A1 | 3/2009 | Folden et al. |
| 2009/0151864 A1 | 6/2009 | Burke et al. |
| 2009/0203973 A1 | 8/2009 | Donoghue et al. |
| 2009/0305315 A1 | 12/2009 | Gandola et al. |
| 2009/0308185 A1 | 12/2009 | Wu et al. |
| 2009/0320684 A1 | 12/2009 | Weaver et al. |
| 2010/0015611 A1 | 1/2010 | Webster et al. |
| 2010/0229956 A1 | 9/2010 | Luyendijk |
| 2010/0331219 A1 | 12/2010 | Munenaka |
| 2011/0003330 A1 | 1/2011 | Durack |
| 2011/0124098 A1 | 5/2011 | Rose et al. |
| 2011/0151432 A1 | 6/2011 | Zappia et al. |
| 2011/0294112 A1 | 12/2011 | Bearinger et al. |
| 2011/0294205 A1 | 12/2011 | Hukari et al. |
| 2012/0100624 A1 | 4/2012 | Hara et al. |
| 2012/0105837 A1* | 5/2012 | Ingber ................ G01N 21/6452 356/246 |
| 2012/0285562 A1 | 11/2012 | Richardson |
| 2013/0003162 A1 | 1/2013 | Leoni et al. |
| 2013/0130232 A1 | 5/2013 | Weibel et al. |
| 2013/0244241 A1 | 9/2013 | Carrera Fabra et al. |
| 2013/0266948 A1 | 10/2013 | Bird et al. |
| 2013/0295663 A1 | 11/2013 | Weight et al. |
| 2013/0323738 A1 | 12/2013 | Tanner et al. |
| 2013/0323793 A1 | 12/2013 | Tanner et al. |
| 2014/0031248 A1 | 1/2014 | Tanner et al. |
| 2014/0057268 A1 | 2/2014 | Tanner et al. |
| 2014/0073043 A1 | 3/2014 | Holmes |
| 2014/0188089 A1 | 7/2014 | Midgette et al. |
| 2014/0228773 A1 | 8/2014 | Burkholz |

(56) References Cited

U.S. PATENT DOCUMENTS

| | | | |
|---|---|---|---|
| 2014/0242612 A1 | 8/2014 | Wang et al. | |
| 2014/0335505 A1* | 11/2014 | Holmes | G06F 19/366 |
| | | | 435/5 |
| 2014/0356874 A1 | 12/2014 | Bearinger | |
| 2015/0024436 A1 | 1/2015 | Eberhart et al. | |
| 2015/0111201 A1 | 4/2015 | Ozcan et al. | |
| 2015/0132795 A1 | 5/2015 | Griswold et al. | |
| 2015/0151300 A1 | 6/2015 | Williams et al. | |
| 2015/0182966 A1 | 7/2015 | Coursey | |
| 2015/0240293 A1 | 8/2015 | Tanner et al. | |
| 2015/0247190 A1 | 9/2015 | Ismagilov et al. | |
| 2015/0298118 A1 | 10/2015 | Chard et al. | |
| 2015/0321193 A1 | 11/2015 | Sprague et al. | |
| 2015/0328638 A1 | 11/2015 | Handique et al. | |
| 2015/0359458 A1 | 12/2015 | Erickson et al. | |
| 2016/0077015 A1* | 3/2016 | Holmes | G01N 33/50 |
| | | | 506/9 |
| 2016/0194685 A1 | 7/2016 | Unger et al. | |
| 2016/0216287 A1* | 7/2016 | Holmes | G01N 35/00 |
| 2016/0275149 A1 | 9/2016 | Majumdar et al. | |
| 2016/0334403 A1 | 11/2016 | Gibbons et al. | |
| 2017/0044599 A1 | 2/2017 | Mitra et al. | |
| 2018/0293350 A1 | 10/2018 | Dimov et al. | |
| 2019/0060895 A1 | 2/2019 | Myers, III et al. | |
| 2019/0076841 A1 | 3/2019 | Myers, III et al. | |
| 2019/0083975 A1 | 3/2019 | Mitra et al. | |
| 2019/0094114 A1 | 3/2019 | Myers, III et al. | |
| 2019/0309356 A1 | 10/2019 | Mitra et al. | |
| 2019/0314810 A1 | 10/2019 | Khattak et al. | |
| 2020/0030798 A1 | 1/2020 | Mitra et al. | |
| 2020/0122142 A1 | 4/2020 | Myers, III et al. | |
| 2020/0164373 A1 | 5/2020 | Khattak et al. | |

FOREIGN PATENT DOCUMENTS

| | | |
|---|---|---|
| CN | 104937108 A | 9/2015 |
| CN | 105441312 A | 3/2016 |
| CN | 201930535293.7 | 4/2020 |
| EP | 0056241 A1 | 7/1981 |
| EP | 0520408 A2 | 12/1992 |
| EP | 1661988 A1 | 5/2006 |
| EP | 2251435 A1 | 11/2010 |
| JP | 2008-173218 A | 7/2008 |
| JP | 2010-538801 A | 12/2010 |
| JP | 2013-526867 A | 6/2013 |
| JP | 2013-532488 A | 8/2013 |
| WO | 1997/012681 A1 | 4/1997 |
| WO | 1997/041421 A1 | 11/1997 |
| WO | 2004/024892 A2 | 3/2004 |
| WO | 2005/012518 A1 | 2/2005 |
| WO | 2008/107014 A1 | 9/2008 |
| WO | 2009/039259 A1 | 3/2009 |
| WO | 2010/091080 A2 | 8/2010 |
| WO | 2011/110873 A1 | 9/2011 |
| WO | 2011/123064 A1 | 10/2011 |
| WO | 2011/144345 A1 | 11/2011 |
| WO | 2012/018741 A2 | 2/2012 |
| WO | 2012/045889 A1 | 4/2012 |
| WO | 2013/008042 A1 | 1/2013 |
| WO | 2013/080154 A1 | 6/2013 |
| WO | 2014/018828 A1 | 1/2014 |
| WO | 2014/020326 A2 | 2/2014 |
| WO | 2014/031783 A1 | 2/2014 |
| WO | 2014/144548 A1 | 9/2014 |
| WO | 2015/164770 A1 | 10/2015 |
| WO | 2015/184360 A1 | 12/2015 |
| WO | 2017/160836 A1 | 9/2017 |
| WO | 2017/160838 A1 | 9/2017 |
| WO | 2017/160839 A1 | 9/2017 |
| WO | 2017/160840 A1 | 9/2017 |
| WO | 2018/140540 A1 | 8/2018 |
| WO | 2018/185573 A1 | 10/2018 |
| WO | 2019/055135 A1 | 3/2019 |

OTHER PUBLICATIONS

Canadian Office Action for Application No. 2,944,994, dated Aug. 8, 2019, 3 pages.
Cao et al., "Microfluidic Chip for Molecular Amplification of Influenza A RNA in Human Respiratory Specimens," PLoS One, Mar. 2012, vol. 7, Issue 3, pp. 1-11.
European Application No. 17767336.5, Extended European Search Report dated Sep. 26, 2019, 14 pages.
European Application No. 17767337.3, Extended European Search Report dated Sep. 18, 2019, 6 pages.
European Application No. 17767339.9, Extended European Search Report dated Oct. 4, 2019, 11 pages.
European Search Report for European Patent Application No. EP 19178796.9, dated Oct. 9, 2019, 7 Pages.
European Search Report, International Application No. EP18780624, dated Dec. 4, 2020, 10 pages.
Foo et al., "Rapid Tests for the Diagnosis of Influenza," Australian Prescriber, vol. 32, No. 3, Jun. 2009, pp. 64-67.
Goto., M., et al., "Colorimetric detection of loop-mediated isothermal amplification reaction by using hydroxy naphthol blue", Biotechniques, Mar. 1, 2009, pp. 167-172, vol. 46, No. 3.
Non-Final Office Action for U.S. Appl. No. 15/306,240, dated Jul. 24, 2018, 8 pages.
Non-Final Office Action for U.S. Appl. No. 16/359,913, dated Oct. 1, 2019, 9 pages.
Non-Final Office Action for U.S. Appl. No. 29/674,581, dated Jan. 8, 2020, 11 pages.
Partial Supplemental European Search Report for European Patent Application No. EP 17767338.1, dated Oct. 10, 2019, 15 Pages.
Patent Cooperation Treaty, International Search Report and Written Opinion of the International Searching Authority, International Patent Application No. PCT/US19/55365, dated Feb. 5, 2020, 20 Pages.
Patent Cooperation Treaty, International Search Report and Written Opinion of the International Searching Authority, International Patent Application No. PCT/US2015/027556, dated Sep. 15, 2015, 18 Pages.
Patent Cooperation Treaty, International Search Report and Written Opinion of the International Searching Authority, International Patent Application No. PCT/US2017/022300, dated Jul. 10, 2017, 15 Pages.
Patent Cooperation Treaty, International Search Report and Written Opinion of the International Searching Authority, International Patent Application No. PCT/US2017/022304, dated Jul. 25, 2017, 20 Pages.
Patent Cooperation Treaty, International Search Report and Written Opinion of the International Searching Authority, International Patent Application No. PCT/US2017/022305, dated Jul. 19, 2017, 20 Pages.
Patent Cooperation Treaty, International Search Report and Written Opinion of the International Searching Authority, International Patent Application No. PCT/US2017/022306, dated Jun. 5, 2017, 18 Pages.
PCT International Search Report and Written Opinion for PCT/IB2018/051326, dated Jun. 26, 2018, 15 pages.
PCT International Search Report and Written Opinion for PCT/US2018/044044, dated Sep. 26, 2018, 13 Pages.
Supplementary European Search Report for European Patent Application No. EP 15783787, dated Nov. 28, 2017, 8 Pages.
Supplementary European Search Report for European Patent Application No. EP 17767338.1, dated Jan. 10, 2020, 13 Pages.
Westcott, S.L., et al., "Broadband optical absorbance spectroscopy using a whispering gallery mode microsphere resonator," Review of Scientific Instruments, vol. 79, No. 3, Mar. 13, 2008, 9 Pages.

\* cited by examiner

Receive a set of images of an optical property modifying device for a nucleic acid disease diagnostic test captured by an optical sensor of a mobile device.
610

For each image in the set, determine whether the surface of the optical property modifying device is shown in the image.
620

Select one or more images of the set that are determined to show the surface.
630

Determine a test result for the nucleic acid disease diagnostic test based on the one or more images.
640

Provide the test result for display on the mobile device.
650

FIG. 6

IMAGE-BASED DISEASE DIAGNOSTICS USING A MOBILE DEVICE

CROSS-REFERENCE TO RELATED APPLICATION

This application is a continuation-in-part of U.S. patent application Ser. No. 15/481,349, filed Apr. 6, 2017, now U.S. Pat. No. 10,146,909, which is incorporated by reference herein in its entirety for all purposes.

BACKGROUND

1. Field of Art

This description generally relates to disease diagnostics, and particularly to a portable system to perform image-based disease diagnostic tests.

2. Description of the Related Art

Though many disease diagnostic tests are performed in laboratory settings using benchtop equipment, advances in medical technologies such as microfluidics have enabled users to perform diagnostic tests using smaller-sized and more portable equipment. For example, the hardware required to complete an immunoassay for a diagnostic test can be fit into a handheld device. However, in conventional test processes, trained personnel such as a nurse, physician, or lab technician must analyze the handheld device to determine the test result. Thus, a patient would have to visit a facility such as a healthcare clinic, or the trained personnel would have to visit the patient at the patient's home, for example. Alternatively, the patient can collect a biological sample of the patient (such as a mouth or nostril swab) at the patient's home and mail the biological sample to a laboratory to perform the immunoassay using the biological sample.

The above examples may not provide a quick test result because these processes require travel of person(s) or transportation of some test material. Additionally, in remote areas that have scarce medical resources and personnel, it is especially challenging to perform diagnostic tests using conventional test processes. Developments in telecommunications have helped spur the growth of telemedicine technologies that provide remote diagnosis of patients. However, it is still challenging to perform a point-of-care diagnostic test using a reliable and portable end-to-end system that patients can complete in the comfort of their homes.

SUMMARY

A diagnostic system performs disease diagnostic tests (also referred to herein as a "diagnostic test" or a "nucleic acid disease diagnostic test") using at least an optical property modifying device and a mobile device. A user provides a biological sample from a patient to the optical property modifying device that reacts with an optical property modifying reagent in reaction chambers of the device. For example, the optical property modifying device performs a nucleic acid amplification assay that changes the color of a solution including the biological sample and the optical property modifying reagent in the reaction chambers. The user captures one or more images of the reaction chambers using an optical sensor (e.g., camera) of the mobile device. To help the user align the mobile device to the reaction chambers, the optical property modifying device or a user interface displayed on the mobile device can provide visual markers. The diagnostic system can determine a quality level of the images based on factors such as skew, scale, focusing, shadowing, or white-balancing. The diagnostic system determines whether to select an image for further analysis based on the corresponding quality level.

The diagnostic system analyzes one or more selected images to determine a test result of a disease diagnostic test for the patient. For example, based on known reference information, the diagnostic system matches a color change of the reaction chambers to a particular test result, for instance, positive, negative, or undetermined. The diagnostic system may communicate the test result, as well as instructions for the disease diagnostic test, to the user via the mobile device. The diagnostic system can also provide the test result and relevant metadata to other health care providers such as a physician or a pharmacy to provide suitable treatment if the patient tests positive for a disease.

Thus, the diagnostic system is a point-of-care system that enables patients to conveniently complete disease diagnostic tests at their homes (or other patient locations) without having to leave their homes, mail test material to a lab, or have a health care personnel visit them at their homes. The optical property modifying device, mobile device, and any other required test equipment, such as a swab and collection tube for the biological sample, are all portable. Since the mobile device (or a computer server in communication with the mobile device) performs image analysis to determine the test result, the diagnostic system can provide a quick diagnosis without requiring any input from health care personnel. Further, test results of the diagnostic system are mobile device hardware-independent because the diagnostic system can normalize images captured from different types of mobile devices and optical sensors.

In one embodiment, a method receives at least one image of an optical property modifying device for a nucleic acid disease diagnostic test captured by an optical sensor of a mobile device of a user. The optical property modifying device includes a plurality of reaction chambers on a surface of the optical property modifying device and configured to react a biological sample with an optical property modifying reagent. For each image of the at least one image, the method determines whether the surface of the optical property modifying device is shown in the image based on at least one of a known geometric characteristic and a known color characteristic associated with the surface of the optical property modifying device. The method selects one or more images of the at least one image that are determined to show the surface. The method determines a test result for the nucleic acid disease diagnostic test based at least in part on the one or more images and at least one of the reaction chambers. The method provides the test result for display on an electronic display of the mobile device.

In some embodiments, the method provides the test result, a geographical location of the mobile device, and a timestamp of the geographical location to a computer server, which compiles epidemiological data based on aggregated test results. In some embodiments, the method provides information associated with the test result to a pharmacy to allow the pharmacy to fulfill a prescription for a patient. In some embodiments, the method generates a message including sponsored content based on the test result and provides the message to the mobile device. In some embodiments, the method provides the test result to a health care provider located within a predetermined distance from the patient and provides a recommendation from the health care provider to treat the disease. In some embodiments, the method provides the test result to a computer server of a third party including health information based on aggregated test results for a population of patients. In some embodiments, the sensitivity and specificity of the test results are adjusted to account for geospatial and seasonal variations in disease prevalence.

Since a patient can complete the chemical reaction portion of the disease diagnostic test at home using the optical property modifying device, the diagnostic system and methods described herein do not require a central lab to perform disease diagnostic tests. Further, the diagnostic system may provide test results and related information directly to a pharmacy or other health care providers.

In another embodiment, a non-transitory computer-readable storage medium stores instructions that when executed by a processor causes the processor to execute the above-described method.

BRIEF DESCRIPTION OF DRAWINGS

Figure (FIG. 1 is a diagram of a system environment for performing disease diagnostic tests according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Example System Overview

Figure 1:
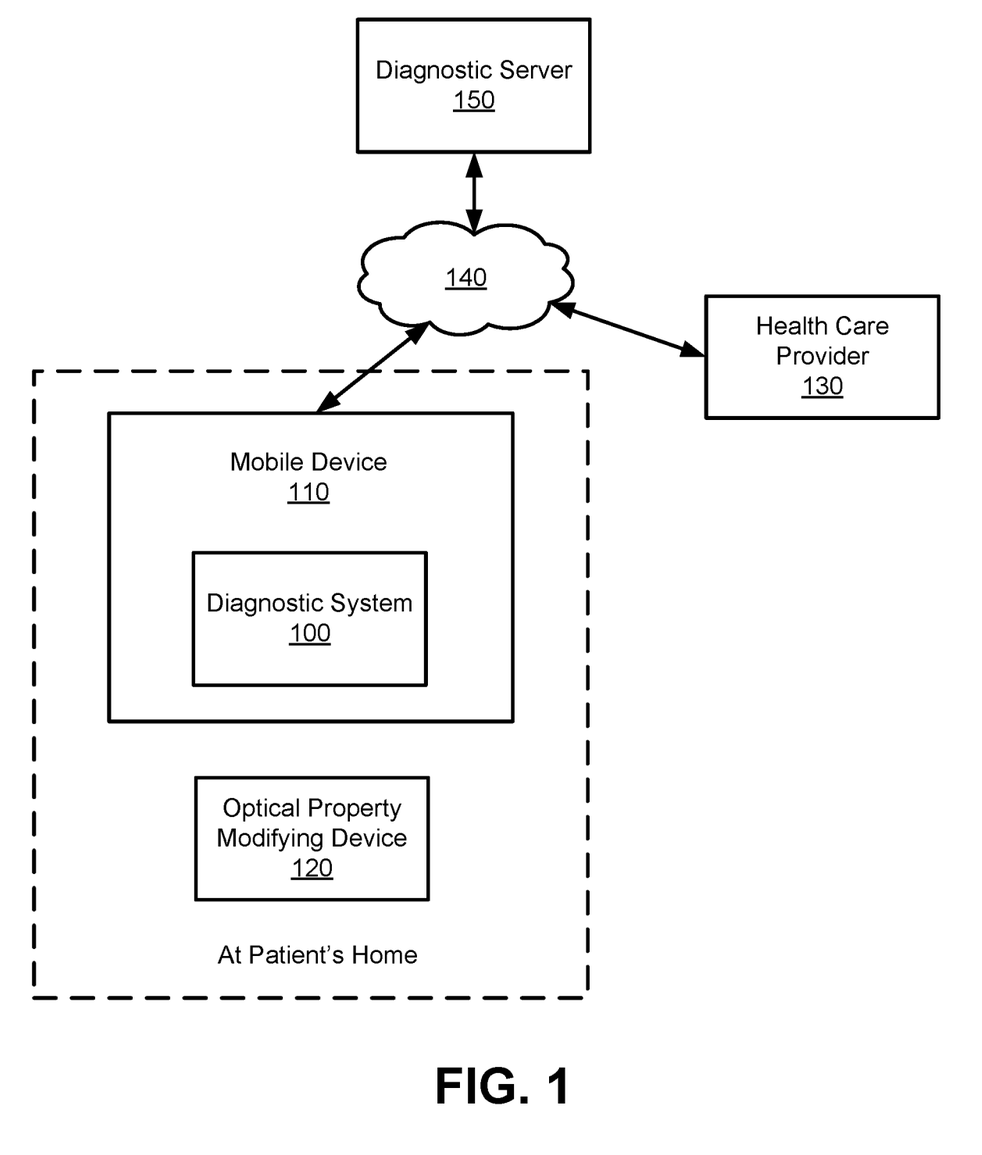

FIG. 1 is a diagram of a system environment for performing disease diagnostic tests according to one embodiment. The system environment includes a diagnostic server 150, a mobile device 110, an optical property modifying device 120, and one or more health care providers 130. The diagnostic server 150, mobile device 110, and health care providers 130 can be connected to each other via a network 140. In other embodiments, different and/or additional entities can be included in the system environment. The functions performed by the various entities of FIG. 1 may vary in different embodiments.

The mobile device 110 is an electronic device that includes a diagnostic system 100 to determine test results for disease diagnostic tests performed by users using at least the mobile device 110 (e.g., a smartphone, tablet, laptop computer, etc.) and optical property modifying device 120. Since the mobile device 110 and optical property modifying device 120 are portable, users can perform disease diagnostic tests at the patient's home or any other suitable location outside of health care facilities such as hospitals or central labs for disease diagnostic tests. The diagnostic server 150 is a computer server that can perform some or all functionality of the diagnostic system 100 in some embodiments.

A user of the mobile device 110 interacts with the diagnostic system 100 via a mobile application. The mobile application communicates information from the diagnostic system 100. For example, the mobile application presents instructions or results for a disease diagnostic test on a graphical user interface displayed on an electronic display on the mobile device 110. As another example, the mobile application provides information via audio signals or tactile feedback (e.g., vibrating the mobile device 110). The mobile application running on the mobile device 110 can provide data from sensors of the mobile device 110 the diagnostic system 100. For example, the mobile device 110 includes an optical sensor such as a camera to capture images of the optical property modifying device 120. The mobile device 110 can provide the captured images to the diagnostic system 100 for further processing, which is further described with reference to FIG. 3. As other examples, the mobile device 110 may also include a Global Positioning System (GPS) sensor, motion sensors (e.g., accelerometer, gyroscope, or inertial measurement unit), proximity sensors, or temperature sensors.

The mobile device 110 can communicate with the diagnostic server 150 and health care providers 130 via the network 140, which may comprise any combination of local area and wide area networks employing wired or wireless communication links. In one embodiment, the network 140 uses standard communications technologies and Internet protocols. In some embodiments, all or some of the communication links of the network 140 may be encrypted, for example, to provide a technical safeguard for Health Insurance Portability and Accountability Act (HIPAA) compliance.

The health care provider 130 is a computer server associated a health care provider such as a pharmacy, a central laboratory (e.g., for completing chemical reactions for disease diagnostic tests), a hospital, other types of healthcare facilities, or any other suitable provider of health care services. As an example use case, the diagnostic system 100 provides a disease diagnostic test result of a patient to a pharmacy. Based on the results, the pharmacy determines an appropriate prescription for the patient.

Figure 2A:
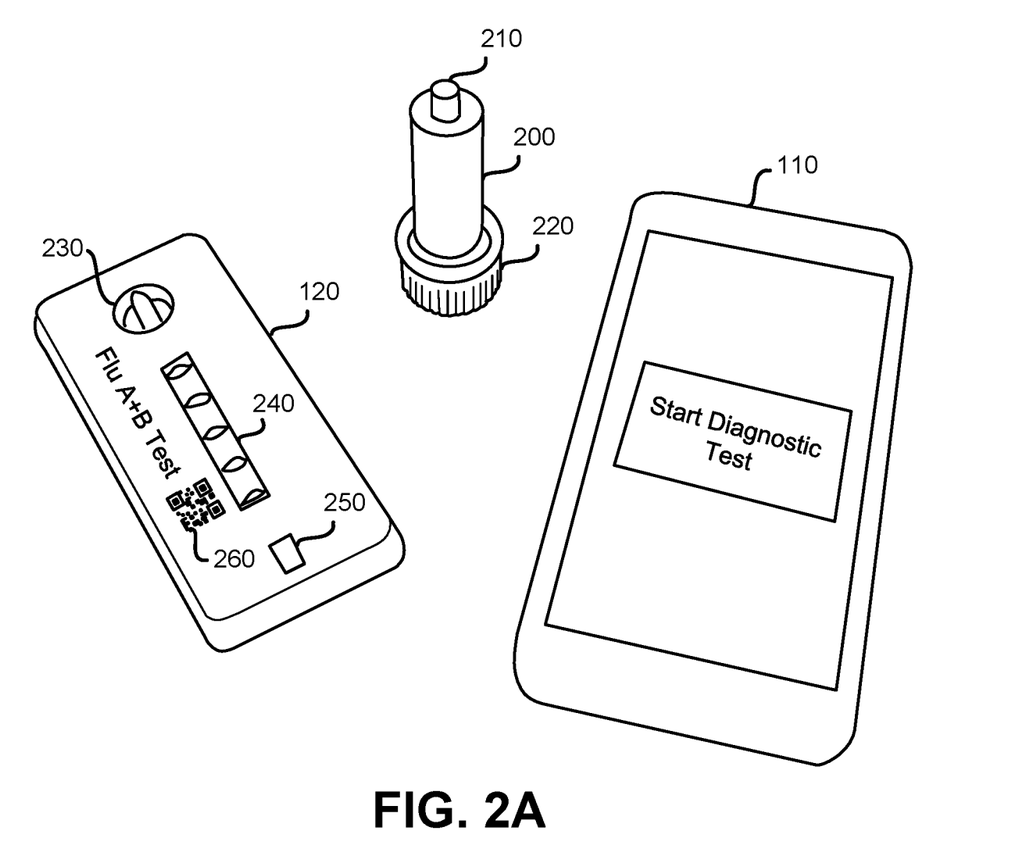
FIG. 2A is a diagram of an optical property modifying device for use with a mobile device according to one embodiment.

FIG. 2A is a diagram of the optical property modifying device 120 for use with a mobile device 110 according to one embodiment. In the embodiment shown in FIG. 2A, the optical property modifying device 120 (also referred to herein as a "cartridge") includes a collection tube interface 230, one or more reaction chambers 240, an indicator 250, and a QR code 260. To perform a disease diagnostic test, a user uses the optical property modifying device 120 to react a biological sample (e.g., including a nucleic acid) of a patient with an optical property modifying reagent in the reaction chambers 240. The reaction chambers 240 are at least partially visible from a surface of the optical property modifying device 120. The optical property modifying device 120 can receive the biological sample from a collection tube 200 via the collection tube interface 230. While performing the disease diagnostic test, the mobile device 110 may provide instructions for the test to the user, for example, via graphical user interfaces further described with reference to FIGS. 4A-H.

The indicator 250 may be a light-emitting diode (LED) that provides an indication of a status of a disease diagnostic test being performed by the optical property modifying device 120. For example, the indicator 250 provides a red colored light indicating that the test has not yet started, a yellow colored light indicating that the test is in progress, and a green colored light indicating that the test has completed. In other embodiments, the indicator 250 may be another type of indicator different than an LED (e.g., an audio indicator) and the optical property modifying device 120 may include any number of indicators 250 (including zero).

The QR code 260 may be associated with information for a disease diagnostic test such as a type of the test or expiration date of the test. The diagnostic system 100 can determine the information for disease diagnostic test by processing images of the QR code 260 scanned by an optical sensor of the mobile device 110. The QR code 260 can also be another type of code, such as a barcode, or other identifier or machine-readable signature.

In one use case, the optical property modifying device 120 performs a type of disease diagnostic test involving nucleic acid(s), e.g. nucleic acid amplification, using the reaction chambers 240 to determine the presence or amount of a particular genetic target in the biological sample. For example, the optical property modifying device 120 includes an optical property modifying reagent, which is a solution comprising nucleic acid enzymes and primers which specifically a target nucleic acid sequence specific to an organism of interest. The presence or amount of this target nucleic acid sequence within the biological sample may indicate that a patient is infected with a particular pathogen or carries a particular genetic disease. Further, the optical property modifying reagent includes a dye which changes color or fluoresces upon target amplification, resulting in a visible change in the solution's optical properties. Thus, the diagnostic system 100 can analyze the optical properties of the solution of the biological sample and the optical property modifying reagent to determine results of the disease diagnostic test. In some embodiments, the optical property modifying device 120 can perform other tests such as immunoassays or enzyme-linked immunosorbent assays (ELISAs).

An optical property modifying device 120 may perform multiple disease diagnostic tests in parallel or in series. The optical property modifying device 120 shown in the example in FIG. 2A includes five reaction chambers 240 (in other embodiments, the number of reaction chambers may vary). Each reaction chamber may or may not be coupled to another reaction chamber. Further, a given disease diagnostic test can be associated with one or more reaction chambers. For example, the optical property modifying device 120 shown in FIG. 2A is used to perform an influenza type A test associated with two of the reaction chambers, an influenza type B test associated with one of the reaction chambers, a positive internal control test associated with one of the reaction chambers, and a negative internal control test associated with one of the reaction chambers. In some embodiments, multiple tests are associated with at least one common reaction chamber, which may be advantageous to consolidate the number of reaction chambers required for the optical property modifying device 120.

Though not shown in FIG. 2A, in some embodiments, the optical property modifying device 120 includes a user control such as a tab, a button, or a switch. The optical property modifying device 120 starts the chemical reaction of the disease diagnostic test when the user interacts with the user control. For example, when the user pulls the tab, presses the button, or activates the switch, the optical property modifying device 120 starts to mix the optical property modifying reagent with the biological sample and regulate temperature of the reaction chambers to an appropriate set temperature point. In other embodiments, the optical property modifying device starts mixing and regulating temperature of the reaction chambers automatically once a biological sample is presented.

The collection tube 200 is configured to store a biological sample and includes a cartridge interface 210 and a cap 220. A user can provide a biological sample to the collection tube 200 using a swab, for example. The cap 220 encloses the biological sample in the collection tube 200. A user can attach the collection tube 200 to the optical property modifying device 120 by physically contacting the cartridge interface 210 of the collection tube 200 to the collection tube interface 230 of the optical property modifying device 120. When attached, the collection tube 200 can provide a stored biological sample to the optical property modifying device 120 via the interfaces 210 and 230. Though the collection tube 200 shown in FIG. 2A is a cylindrical tube, in other embodiments, the collection tube 200 may have a different overall shape or form factor such as a rectangular prism.

Figure 2B:
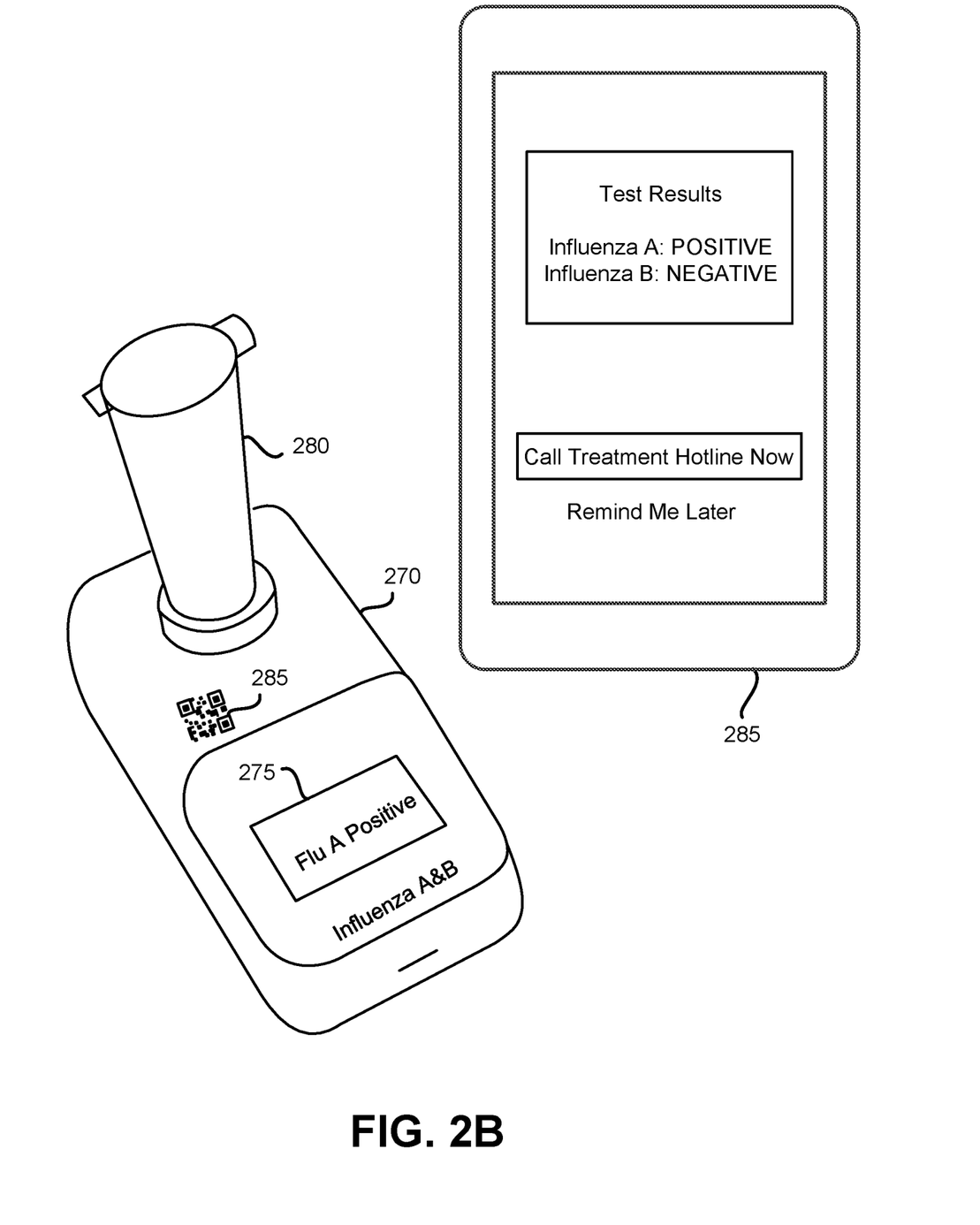
FIG. 2B is a diagram of another optical property modifying device for use with a mobile device according to one embodiment.

FIG. 2B is a diagram of another optical property modifying device for use with a mobile device according to one embodiment. In the example shown in FIG. 2B, the optical property modifying device 270 includes an electronic display 275 on a surface. The electronic display 275 may be, for example, a liquid crystal display (LCD), organic light emitting diode (OLED) display, electronic paper display, or one or more individual light emitting diodes (LEDs), among other types of displays. The electronic display 275 may provide one or more results for presentation on an electronic readout or analysis of one or more properties (e.g., optical, color, or geometric) of at least one reaction chamber within the optical property modifying device 270. The electronic display 275 may provide a result using human-readable symbols (e.g., alphanumeric characters or graphics) or machine-readable symbols (e.g., a barcode or QR code). The result may be based on a reaction using samples from the collection tube 280 within one of the reaction chambers. Additionally, the optical property modifying device 270 may include a QR code 285 on a surface that may be used to identify the optical property modifying device 270 as a test for influenza A & B.

In an embodiment, a mobile device 285 reads and interprets information (e.g., test results) presented by the electronic display 275 using an onboard camera or another type of sensor. Furthermore, the mobile device 285 may use image recognition processes to determine geometric, color, or other visual attributes of the information presented, e.g., for interpreting a diagnostic result from the optical property modifying device 270. The image recognition processes may include, for example, optical pattern matching or optical character recognition (OCR) algorithms known to one skilled in the art. As shown in FIG. 2B, the mobile device 285 may be positioned over the optical property modifying device 270 to scan or take a photo or video of the surface of the optical property modifying device 270 having the electronic display 275. The mobile device 285 may detect that the optical property modifying device 270 presents a message indicating a positive diagnosis for influenza A. Responsive to the detection, the mobile device 285 may provide further interpretation or options for next steps to a user.

II. Example System Architecture

Figure 3:
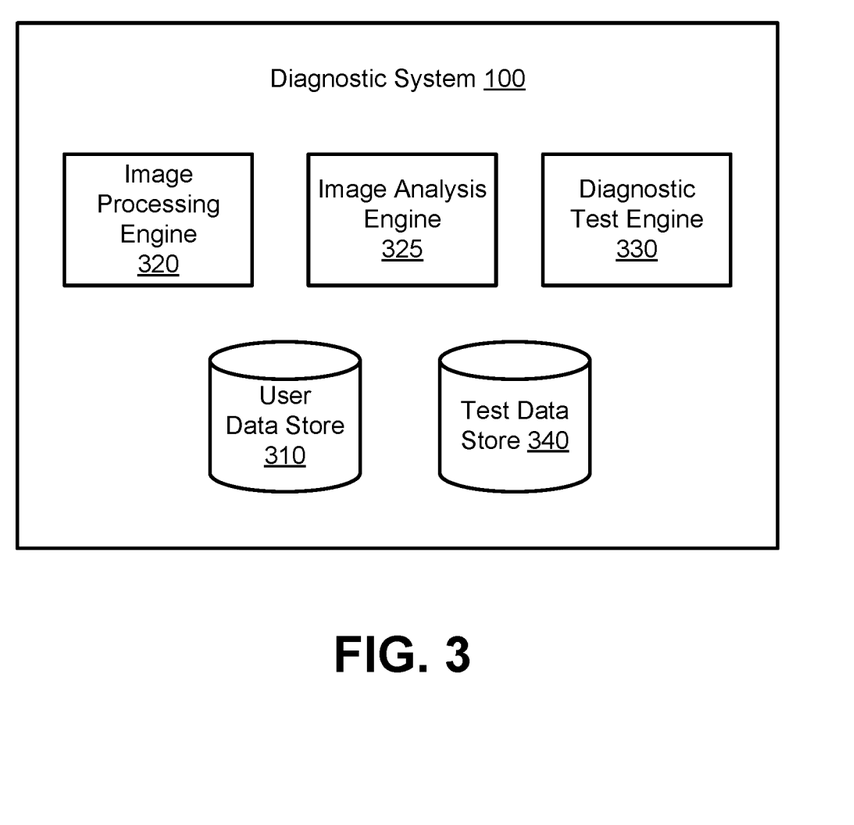
FIG. 3 is a block diagram of a diagnostic system according to one embodiment.

FIG. 3 is a block diagram of a diagnostic system 100 according to one embodiment. The diagnostic system 100 includes a user data store 310, image processing engine 320, image analysis engine 325, diagnostic test engine 330, and test data store 340. In other embodiments, the diagnostic system 100 may include additional, fewer, or different components for various applications.

In some embodiments, some or all of the functionality of the diagnostic system 100 may be performed by or implemented on the diagnostic server 150 instead of the mobile device 110. For example, the mobile device 110 acquires images of an optical property modifying device 120 using the image processing engine 320 and provides the images to the diagnostic server 150 for further processing by the image analysis engine 325. The mobile device 110 can receive a test result determined by the diagnostic server 150 and communicate the test result to a user. This may be advantageous because the image analysis engine 325 may require more computational resources relative to the image processing engine 320 or other components of the diagnostic system 100 on the mobile device 110.

The user data store 310 stores information about users of the diagnostic system 100 such as patients who have completed—or will complete—a diagnostic test. The information may include user information such as name, demographics, family data, geographical location, contact information, or physiological data. The information may describe user's medical history such as prescriptions, health conditions, genetic data, visits to health care providers, past or current medical services or interventions received, or previously completed diagnostic tests along with relevant details such as the date that the tests were taken and the test results.

The image processing engine 320 acquires and processes images from a mobile device 110. The image processing engine 320 may implement image processing techniques known to one skilled in the art such as noise reduction using different types of filters, skew correction, resizing, rescaling, rotation, equalization, focusing/sharpening, or edge detection. The image processing engine 320 can determine whether the surface of an optical property modifying device 120 is shown in the image based on various parameters associated with the surface.

A parameter may be a known geometric characteristic of the optical property modifying device 120. For example, the QR code 260 shown in FIG. 2A is unique to the optical property modifying device 120, a batch of optical property modifying devices 120 (e.g., having a certain expiration date based on a manufacturing date), or a particular type of diagnostic test. Other types of geometric characteristic include, for example, a border of the optical property modifying device 120, a two-dimensional (2D) or three-dimensional (3D) barcode, an alignment marker (e.g., the reaction chambers 240, the indicator 250, the example text "Flu A+B Test" shown in FIG. 2A), or any other type of fiducial marker that may be a point of reference in an image.

The image processing engine 320 may transform an acquired image (e.g. translate, skew, scale, or rotate) based on geometric characteristics, or in other words, spatial data of the image determined by the image processing engine 320. Alternatively, the image processing engine 320 may leave the image unchanged but instead transform the coordinates it uses to identify regions of interest for analysis within the image. As an example, a fiducial marker of the optical property modifying device 120 has a reference orientation and/or size. For instance, the QR code 260 shown in FIG. 2A is known to have a length and width of one centimeter (e.g., dimensions of a square) and be orientated with the text "Flu A+B Test" labeled on the optical property modifying device 120. If the image processing engine 320 determines that the QR code 260 appears smaller or larger than expected based on the reference size, the image processing engine 320 can scale the image up or down, respectively. If the image processing engine 320 determines that the QR code 260 shown in an image is skewed in shape (e.g., a trapezoid or rhombus), the image processing engine 320 can adjust the skew of the image so that the QR code 260 is rendered more closely as the expected shape of a square. If the image processing engine 320 determines that the QR code 260 shown in the image is not aligned to the reference orientation (e.g., the image has been rotated by 45, 60, or 90 degrees), the image processing engine 320 can rotate the image to the reference orientation. Further, the image processing engine 320 can determine a level of focus of the image by resolving two or more features of the optical property modifying device 120 such as the QR code 260 and another fiducial marker.

A parameter may also be a known color characteristic of the optical property modifying device 120. For example, the image processing engine 320 has information indicating that the surface (or a fiducial marker) of the optical property modifying device 120 is known to be a certain color(s). As an example use case, the surface of the optical property modifying device 120 is known to have a uniform white color (or approximately white color). However, an image of the optical property modifying device 120 may be tinted with warmer colors (e.g., red) or cooler colors (e.g., blue) depending on lighting conditions when the image was captured. The image processing engine 320 may use white balancing (e.g., color balancing) to determine the lighting conditions of the image and adjust the colors of the image; thus, the image processing engine 320 can properly match the known white color of the surface of the optical property modifying device 120 with the adjusted image. The image processing engine 320 can also use shadowing techniques to remove or otherwise account for shadows in images that may skew the color of certain portions of the images. For instance, the image processing engine 320 measures the uniformity of a known color of the surface of the optical property modifying device 120 to identify shadows in an image.

In some embodiments, the image processing engine 320 continuously monitors images captured by an optical sensor of the mobile device 110. For example, the mobile device 110 displays a live stream of images captured by the optical sensor (e.g., representing the field of view of the optical sensor) to provide a real-time visual guide for a user to align the mobile device 110 with the optical property modifying device 120 being imaged. While monitoring, the image processing engine 320 can determine a quality level of each image. If the quality level of an image meets a threshold level, the image processing engine 320 selects the image for further processing. The image processing engine 320 may determine the quality level and threshold level based on, for instance, the focus, shadowing, white-balancing level, or illumination level of an image.

Further, by adjusting the image using the techniques and parameters described above, the image processing engine 320 can normalize images captured by mobile devices 110 having different technical specifications. This may be advantageous because users may likely have different types of mobile devices 110. For instance, one mobile device has a higher resolution camera with stronger white flash light than another mobile device. By normalizing images captured from these two mobile devices, the image processing engine 320 can effectively process images regardless of the particular specifications of the mobile devices.

The image analysis engine 325 analyzes images acquired and processed by the image processing engine 320. In some embodiments, the image analysis engine 325 analyzes one or more reaction chambers 240 in the image of an optical property modifying device 120. In particular, the image analysis engine 325 determines one or more optical properties of the reaction chambers 240 such as the color, transparency, translucency, opacity, or uniformity of the reaction chambers 240 and/or contents within the reaction chambers 240.

As an example use case, the image analysis engine 325 determines information about the optical properties of the reaction chambers 240, e.g., the average and variance of color of a group of pixels in an image corresponding to each reaction chamber. The image analysis engine 325 may determine the color average and variance (or any other statistical analysis) based on a RGB (red-green-blue) color model, hue-saturation-value (HSV) color model, or any other suitable color model. The image analysis engine 325 identifies these optical properties based on known geometric parameters of the optical property modifying device 120 such as size, shape, orientation, or identifying fiducial marks. For instance, the image analysis engine 325 retrieves a color image (e.g., to use as a reference image) from the test data store 340, identifies the size and orientation of a QR code in the color image, and uses a known size (e.g., 1×1 cm) of the QR code and known relative positions of the five reaction chambers to the QR code (e.g., 2 cm to the right and above, spaced at 1 cm increments) to extract the color average and variance of each reaction chamber.

The image analysis engine 325 can determine test results for a disease diagnostic test by comparing the determined color information of a reaction chamber 240 to reference information that indicates one or more color ranges (e.g., based on the RGB or HSV color model). A color range may correspond to a diagnosis for a disease diagnostic test associated with the reaction chamber 240. Thus, the image analysis engine 325 determines a test result based on the color range within which the determined color of the reaction chamber 240 falls. In other words, the image analysis engine 325 can match color changes of the reaction chambers 240 to a particular test result. For instance, the image analysis engine 325 determines a negative diagnosis of the disease responsive to matching the determined color to a first color range (e.g., yellow to green colors). The image analysis engine 325 determines a positive diagnosis of the disease responsive to matching the determined color to a second color range (e.g., blue to violet colors). The image analysis engine 325 determines an undetermined (e.g., "not available" or "unknown") diagnosis of the disease responsive to matching the determined color to a third color range (or any colors that do not fall within any specified range).

Alternatively, the image analysis engine 325 can determine a test result based on the distribution and clustering of colors of the individual pixels comprising the image of a reaction chamber 240, rather than a point estimate of color average or variance. For example, the image analysis engine 325 can classify each pixel within the image of reaction chamber 240 as falling within one of the three color ranges described above. If a plurality of pixels falls within the first color range, the image analysis engine 325 determines a negative diagnosis of the disease. If a plurality of pixels falls within the second color range, the image analysis engine 325 determines a positive diagnosis of the disease. If a plurality of pixels falls within the third color range, the image analysis engine 325 determines an undetermined diagnosis of the disease. In this way, the image analysis engine 325 is robust to, for example, black and white pixels representing reflections from chamber edges that are substantially different colors from the solution within the reaction chambers 240 and might confound a point estimate-based approach to determining the color of the solution.

In some embodiments, the image analysis engine 325 determines a severity level of the disease or a confidence level of test result based on the comparing the color information with the reference information. For example, relative to a lighter color, a darker color within a certain color range may indicate that the disease diagnosis is more severe or that there is a greater confidence level. An undetermined test result may occur due to various factors such as a defect in the collection tube 200 or optical property modifying device 120, variation in the captured image, or human error by the user or patient, e.g., contaminating the biological sample provided for the diagnostic test or not waiting long enough (or too long) for a chemical reaction of the diagnostic test to complete.

The image analysis engine 325 may also determine test results further based on information other than analyzed images in some embodiments. For example, the image analysis engine 325 determines test results based on a geographical location and/or timestamp of the diagnostic test. In particular, a certain disease may be more prevalent in a certain geographical region (e.g., an area with a tropical climate or a dry climate) or during a certain time range (e.g., during the summer or winter season). In some embodiments, the performance (e.g., sensitivity vs. specificity) of the test can be adjusted based upon known epidemiological factors such as disease prevalence so that during times of low prevalence, the sensitivity of the test can be decreased to prevent false positive test results.

In some embodiments, the image analysis engine 325 implements defect detection algorithms to analyze an image of an optical property modifying device 120. For example, the image analysis engine 325 identifies bubbles in the reaction chambers 240 of the optical property modifying device 120 or other types of defects such as debris or scratches inside or on the exterior of the reaction chambers 240. Based on the identification of a defect, the image analysis engine 325 may use image processing techniques to remove the defects from the image, e.g., removing a cluster of pixels corresponding to a defect. Thus, the image analysis engine 325 can exclude anomalous color values from the determination of color information (e.g., average and variance), which may improve the accuracy of the corresponding test result.

The diagnostic test engine 330 provides information to and/or receives information from mobile devices 110 and health care providers 130 for disease diagnostic tests. For example, the diagnostic test engine 330 receives data from a mobile device 110 such as images of an optical property modifying device 120 captured by an optical sensor of the mobile device 110 and/or metadata such as the geographical location of the mobile device 110, a timestamp of a captured image, or information describing the optical sensor (e.g., pixel resolution, aperture, or flash). The diagnostic test engine 330 determines information for diagnostic tests (e.g., a type of diagnostic test or a result of the diagnostic test) based on images processed and analyzed by the image processing engine 320 and/or the image analysis engine 325.

The diagnostic test engine 330 may provide instructions for a diagnostic test to the mobile device 110 and provide test results of the diagnostic test to the mobile device 110 or a health care provider 130. The diagnostic test engine 330 can retrieve the instructions for the diagnostic test (e.g., including text, graphics, audio, or other media content) from the test data store 340. Further, the diagnostic test engine 330 can store test results in the test data store 340 or the user data store 310 along with relevant information such as the analyzed images of the optical property modifying device 120 and reaction chambers 240, information about the patient who took the diagnostic test, or a geographical location and/or timestamp associated with the diagnostic test.

In some embodiments, the diagnostic test engine 330 can provide test results and associated metadata to a computer server (e.g., a health care provider 130), which can render epidemiological data based on aggregated test results from multiple mobile devices 110 and a population of patients. The epidemiological data may be organized based on various parameters (e.g., demographics, geographical location, temporal information, or types of diseases) and used to determine risk factors or preventative measures for certain diseases.

In some embodiments, the diagnostic test engine 330 may communicate sponsored content based on test results of diagnostic tests to users via the mobile device 110. For instance, the sponsored content is a content item displayed on a user interface of the mobile device 110. Examples of sponsored content include information from vendors of goods or services that may help treat diseases tested by the diagnostic system 100. For instance, the vendors provide prescription medicines, over-the-counter medicines, physical therapy, rehabilitative services, etc.

In some embodiments, the diagnostic test engine 330 can provide test results to a computer server of a third party, e.g., a health provider or a government health organization such as the Centers for Disease Control and Prevention (CDC). The computer server includes aggregated health information of a population of people, and may organize the health information based on geographical location. Thus, for example, the CDC can use the test results and health information to evaluate the well-being of a population within the government's jurisdiction, e.g., monitoring the spread and prevalence of a disease such as influenza.

III. Example User Interfaces of Mobile Application

Figure 4A:
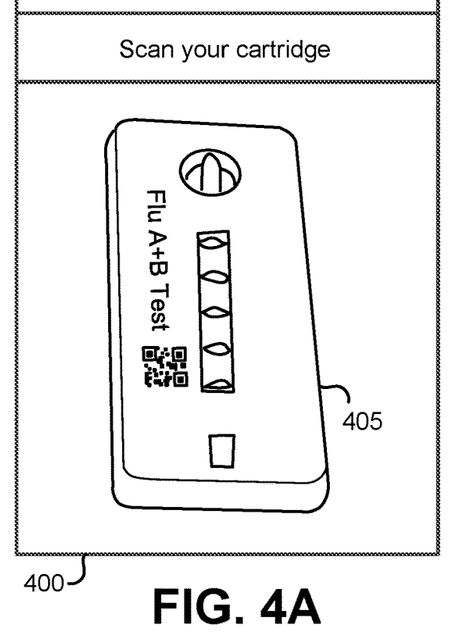
FIG. 4A shows a user interface of a mobile application for a disease diagnostic test according to one embodiment.

FIG. 4A shows a user interface 400 of a mobile application for a disease diagnostic test according to one embodiment. The user interface 400 shows an image 405 of an optical property modifying device 120. The image 405 is the field of view of the camera of the mobile device 110 displaying the user interface 400, for example. The image is oriented to align with the mobile device 110 because the edges of optical property modifying device 120 are approximately parallel to the edges of the user interface 400, and in extension, the mobile device 110. In some embodiments, the user interface 400 includes one or more alignment markers overlaying the field of view to assist a user of the mobile device 110 in aligning the mobile device 110 to the optical property modifying device 120 for capturing the image 405. For example, an alignment marker is a semi-transparent graphic of the optical property modifying device 120 that the user can use to overlap with the physical optical property modifying device 120. As another example, the alignment marker corresponds to a graphic of an element of the optical property modifying device 120 (e.g., the QR code 260), or a line that should be aligned with an edge of the optical property modifying device 120.

Figure 4B:
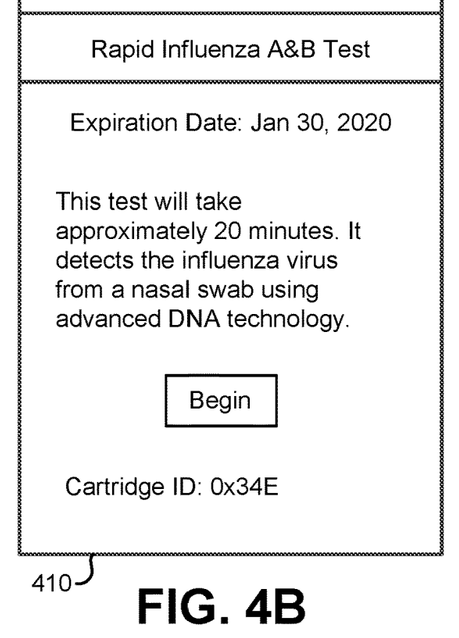
FIG. 4B shows another user interface of the mobile application shown in FIG. 4A including information about the disease diagnostic test according to one embodiment.

FIG. 4B shows another user interface 410 of the mobile application shown in FIG. 4A including information about the disease diagnostic test according to one embodiment. The image processing engine 320 and image analysis engine 325 process the image 405 of the optical property modifying device 120 shown in FIG. 4A. Based on the processing, the diagnostic test engine 330 determines a disease diagnostic test of the optical property modifying device 120 and provides information about the disease diagnostic test for display. In particular, the user interface 410 indicates the type of test (e.g., influenza type A and B), expiration date (e.g., Jan. 30, 2020), test description, duration in time (e.g., 20 minutes for a chemical reaction of the test), and cartridge ID (e.g., 0x34E) of the optical property modifying device 120.

Figure 4C:
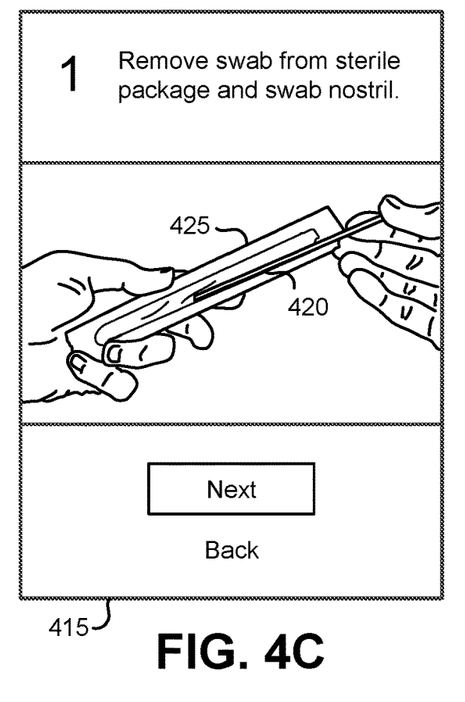
FIG. 4C shows another user interface of the mobile application shown in FIG. 4A including instructions to use a swab according to one embodiment.

FIG. 4C shows another user interface 415 of the mobile application shown in FIG. 4A including instructions to use a swab 420 according to one embodiment. The user interface 415 indicates instructions for an example step of the disease diagnostic test shown in FIG. 4B. For this step, the user is instructed to remove the swab 420 from a sterile package 425 and swab the nostril of a patient undergoing the disease diagnostic test to collect a biological sample of the patient.

Figure 4D:
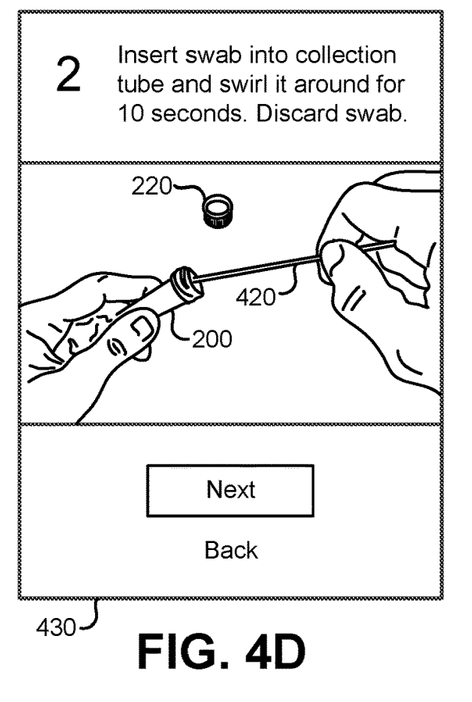
FIG. 4D shows another user interface of the mobile application shown in FIG. 4A including instructions to use a collection tube according to one embodiment.

FIG. 4D shows another user interface 430 of the mobile application shown in FIG. 4A including instructions to use a collection tube 200 according to one embodiment. The user interface 430 indicates instructions for an example step of the disease diagnostic test shown in FIG. 4B. For this step, the user is instructed to insert the swab 420 into the collection tube 200 and swirl the swab 420 around for 10 seconds. Afterwards, the swab 420 should be discarded. The cap 220 of the collection tube 200 is removed so that the swab 420 may be inserted inside.

Figure 4E:
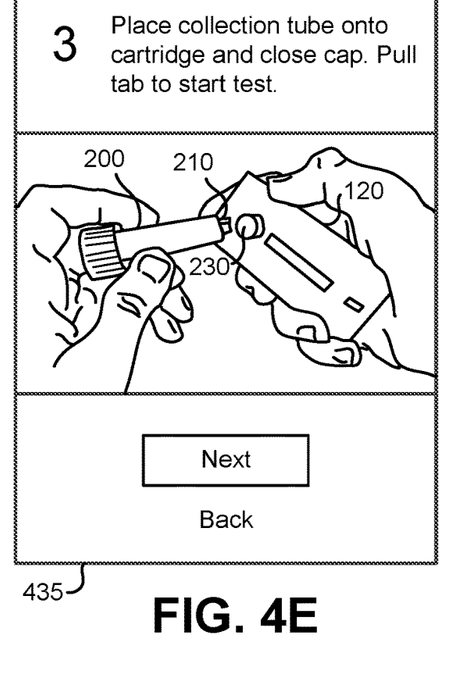
FIG. 4E shows another user interface of the mobile application shown in FIG. 4A including instructions to use a cartridge according to one embodiment.

FIG. 4E shows another user interface 435 of the mobile application shown in FIG. 4A including instructions to use a cartridge according to one embodiment. The user interface 435 indicates instructions for an example step of the disease diagnostic test shown in FIG. 4B. For this step, the user is instructed to place the collection tube 200 onto the cartridge (the optical property modifying device 120) and close the cap 220. In particular, the cartridge interface 210 should be coupled to the collection tube interface 230, which provides the biological sample of the patient to the optical property modifying device 120. The user is also instructed to pull the tab of the optical property modifying device 120 to start the chemical reaction of the disease diagnostic test.

Figure 4F:
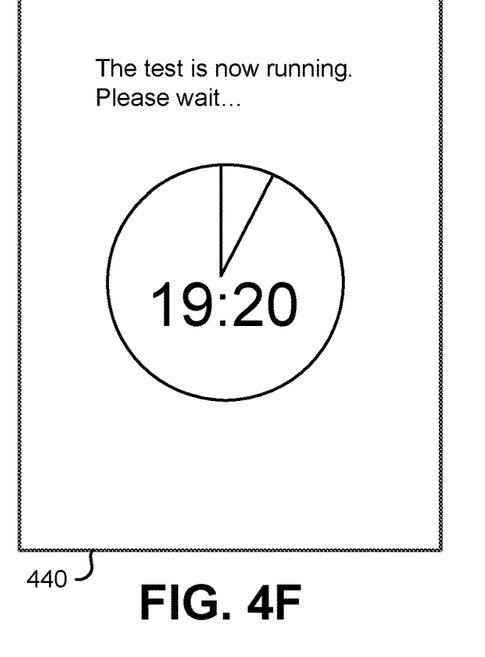
FIG. 4F shows another user interface of the mobile application shown in FIG. 4A including instructions to wait for a chemical reaction of the disease diagnostic test to complete according to one embodiment.

FIG. 4F shows another user interface 440 of the mobile application shown in FIG. 4A including instructions to wait for a chemical reaction of the disease diagnostic test to complete according to one embodiment. The user interface 440 displays a timer that indicates the time remaining until the chemical reaction of the disease diagnostic test shown in FIG. 4B should be complete. Though the total time for this example disease diagnostic test is 20 minutes, in other embodiments, the time may vary, e.g., between 1 and 60 minutes.

Figure 4G:
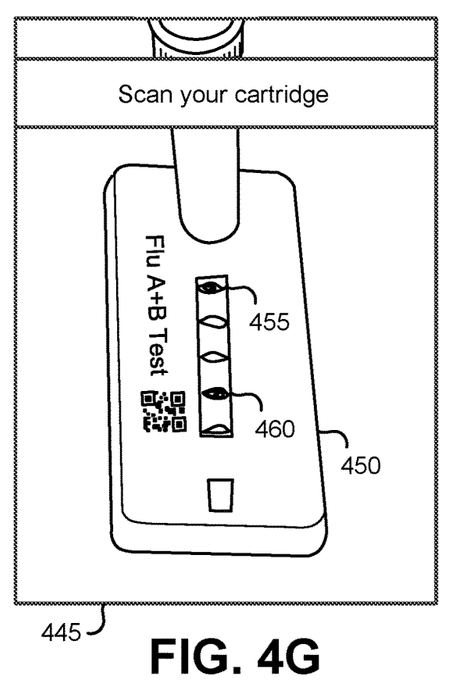
FIG. 4G shows another user interface of the mobile application shown in FIG. 4A including instructions to scan the cartridge according to one embodiment.

FIG. 4G shows another user interface 445 of the mobile application shown in FIG. 4A including instructions to scan the cartridge according to one embodiment. The user interface 445 indicates instructions for an example step of the disease diagnostic test shown in FIG. 4B. For this step, the user is instructed to scan (take one or more images of) the cartridge (the optical property modifying device 120). Since the chemical reaction of the disease diagnostic test has completed after waiting the duration of time for the test, the optical properties of the reaction chambers 240 of the imaged optical property modifying device 120 have changed. Specifically, the image 450 of the optical property modifying device 120 shows that the two of the reaction chambers 455 and 460 have changed at least in color as result of the biological sample of the patient reacting with an optical property modifying reagent.

Figure 4H:
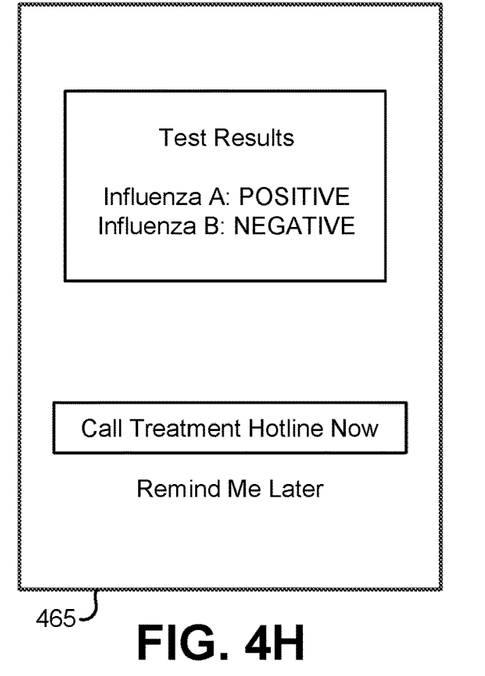
FIG. 4H shows another user interface of the mobile application shown in FIG. 4A including results for the disease diagnostic test according to one embodiment.

FIG. 4H shows another user interface 465 of the mobile application shown in FIG. 4A including results for the disease diagnostic test according to one embodiment. The image processing engine 320 and image analysis engine 325 process and analyze the image 445 of the optical property modifying device 120 shown in FIG. 4G. Based on the analysis, the diagnostic test engine 330 determines test results of the disease diagnostic test and provides information associated with the test results for display on the user interface 465. In particular, the user interface 465 indicates the patient has tested positive for influenza A and negative for influenza B. The user interface 465 also shows an option for the user or patient to call a treatment hotline. For instance, the treatment hotline is a phone number of a health care provider that can provide pharmaceutical drugs or other health care services for treating influenza.

In some embodiments, the user interface 465 provides an option for the user to modify, verify/confirm, or cancel the test result, which may be performed before the diagnostic system 100 provides (via the diagnostic test engine 330) the test result to a health care provider 130, for example. If the test result is updated after the test results has been provided the health care provider 130, the diagnostic test engine 330 may automatically provide the updated test result as well. In one embodiment, if the test result is positive, the diagnostic test engine 330 provides a notification for display on the mobile device 110 indicating that a health care provider will be contacted on behalf of the patient regarding the test result. For example, the diagnostic test engine 330 provides the test result to a physician. The diagnostic test engine 330 may receive a recommendation (e.g., taking vitamins or medication) from the physician in response to providing the test result and communicate the recommendation to the user.

As another example, the diagnostic test engine 330 provides the test result to a pharmacy to allow the pharmacy to fulfill a prescription for the patient to treat the disease associated with the test result. The diagnostic test engine 330 may determine a pharmacy that is located nearby the patient (e.g., within a predetermined distance such as a threshold radius of 10 kilometers) based on geographical information, for instance, the location where the diagnostic test was taken or the address of the patient).

IV. Example Data Flow Diagram

Figure 5A:
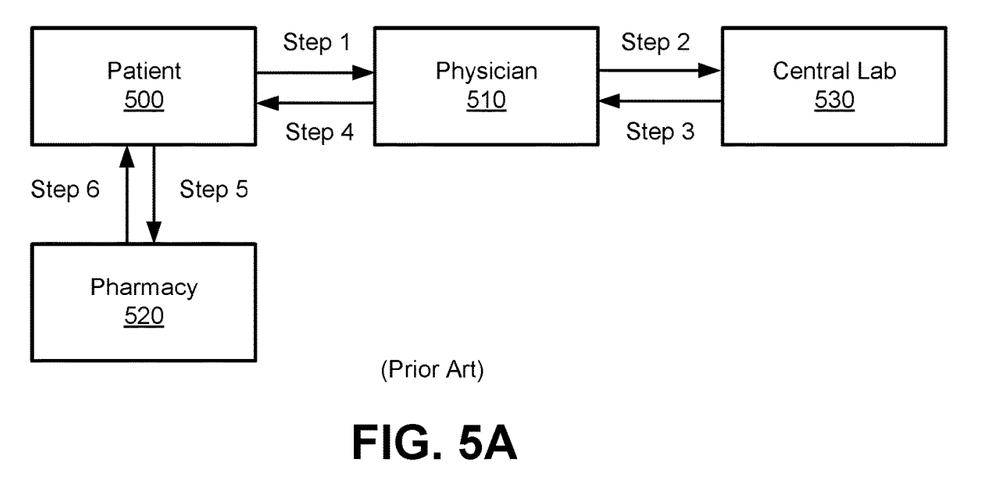
FIG. 5A is a data flow diagram for performing a disease diagnostic test in a conventional system environment according to one embodiment.

FIG. 5A is a data flow diagram for performing a disease diagnostic test in a conventional system environment according to one embodiment. For an example process, in step 1, a patient 500 who wants to complete a disease diagnostic test visits a physician 510 at a hospital or clinic. The physician 510 collects a biological sample of the patient 500. In step 2, the physician 510 provides the biological sample to a central lab 530 with staff that performs the chemical reaction portion of the disease diagnostic test using lab equipment and the biological sample. In step 3, the central lab 530 provides test results of the disease diagnostic test to the physician 510. In step 4, the physician 510 provides the test results to the patient 500. If the patient tested positive for a disease, the test results may indicate a prescription for medication or another type of medical treatment. In step 5, the physician 510 provides the prescription to a pharmacy 520. In some cases, the pharmacy 520 consults with the physician 510 to verify or clarify the prescription. In step 6, the patient 500 visits the pharmacy 520 to request the medication for the prescription. In step 7, the pharmacy 520 fulfills the prescription by providing the medication to the patient 500.

Figure 5B:
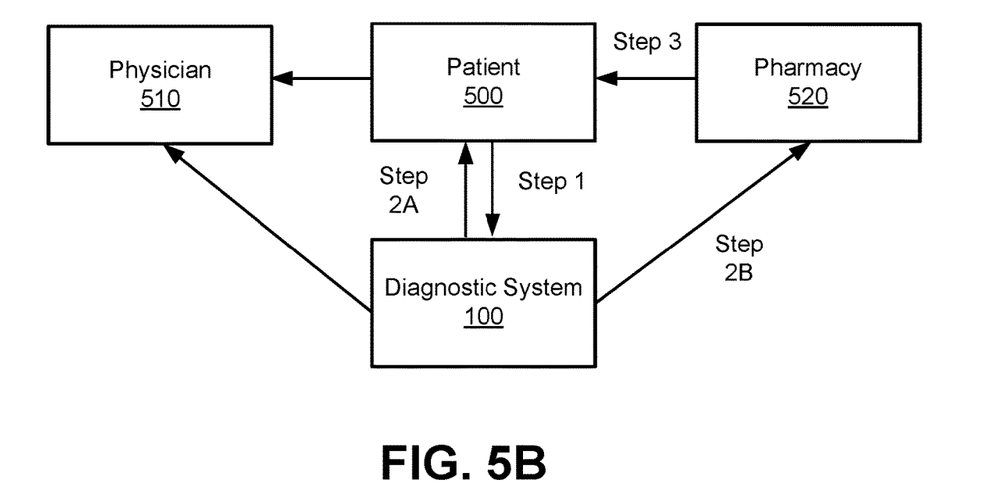
FIG. 5B is a data flow diagram for performing a disease diagnostic test in a system environment including the diagnostic system according to one embodiment.

FIG. 5B is a data flow diagram for performing a disease diagnostic test in a system environment including the diagnostic system 100 according to one embodiment. For an example process, in step 1, a patient 500 who wants to complete a disease diagnostic test uses the diagnostic system 100, e.g., by completing steps of the disease diagnostic test as shown in FIGS. 4A-H. Once the diagnostic system 100 determines test results of the disease diagnostic test, the diagnostic system 100 may simultaneously provide the test results to the patient 500 and the pharmacy 520 in steps 2 A and B. For example, as shown in the FIG. 4H, the diagnostic system 100 provides the test results for display on a user interface of a mobile application. Additionally, the diagnostic system 100 may automatically provide the test results to the pharmacy 520 without requiring further input from the patient 500 (and/or a physician 510), or in response to receiving a confirmation of the test result from the patient 500, in some embodiments. In step 3, the pharmacy 520 fulfills a prescription for the patient 500 based on the test results, e.g., the pharmacy 520 delivers medications to the home of the patient 500 or prepares the medications for pickup at a location nearby the patient 500.

In cases where physician consultation is required, the diagnostic server 150 may consult a physician 510 in an automated manner without requiring that the patient specify the physician or manually facilitate this consultation. In some embodiments, one or more physicians 510 are affiliated with the diagnostic server 150. In some embodiments, the diagnostic system 100 may also provide the test results to the physician 510, e.g., in response to a request by the patient. Thus, if the patient 500 visits the physician 510 to seek treatment for the disease, the physician 510 can determine an appropriate treatment based on the test results.

In contrast to the conventional system environment shown in FIG. 5A, the system environment including the diagnostic system 100 shown in FIG. 5B facilitates a process requiring fewer steps for the patient 500 to complete a disease diagnostic test and receive appropriate medications to treat the disease if the patient 500 tested positive. By reducing the number of steps, the diagnostic system 100 enables patients to receive treatment for diseases more promptly. Further, the system environment shown in FIG. 5B does not require the central lab 530 because the diagnostic system 100 allows the patient 500 to complete the chemical reaction portion of the disease diagnostic test at home using the optical property modifying device 120. This may be particularly advantageous for patients residing far away from the nearest central lab 530, for example, rural areas or developing countries.

V. Example Process Flow

Figure 6:
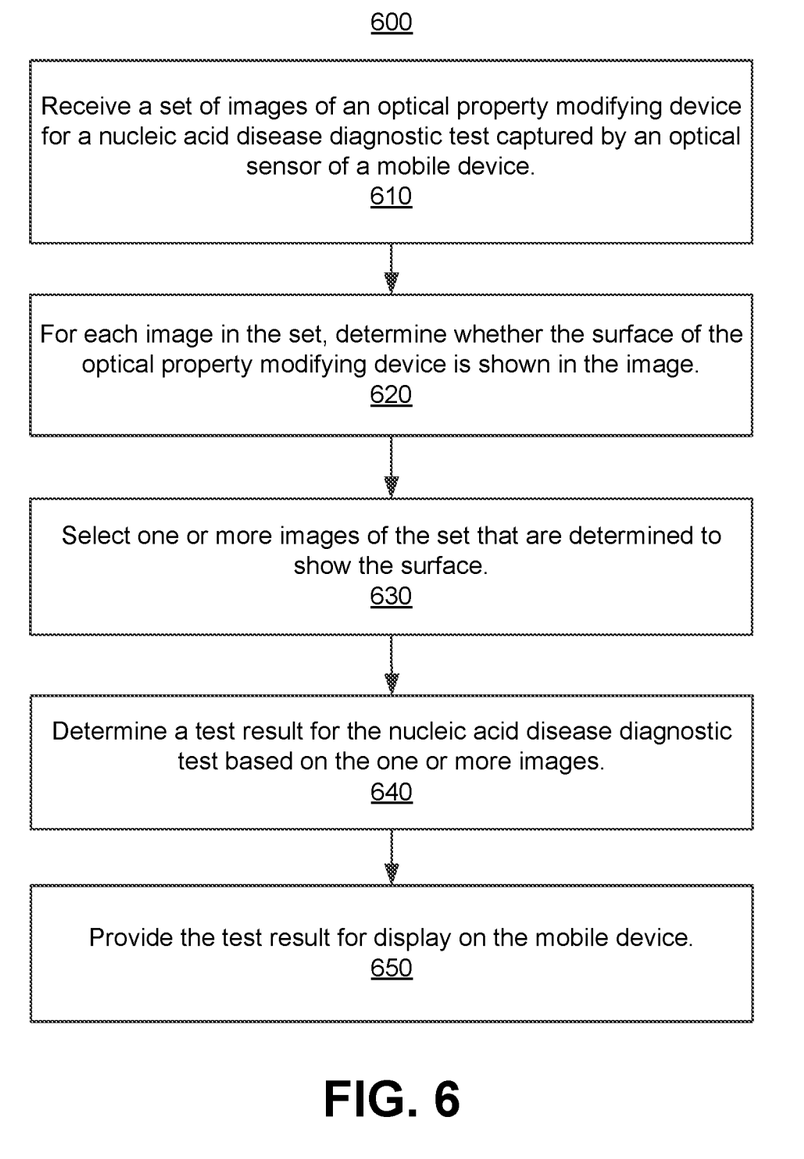
FIG. 6 is a flowchart illustrating a process for determining test results for a disease diagnostic test according to one embodiment.

FIG. 6 is a flowchart illustrating a process 600 for determining test results for a disease diagnostic test according to one embodiment. In some embodiments, the process 600 is used by the diagnostic system 100—e.g., modules of the diagnostic system 100 described with reference to FIG. 3—within the system environment in FIG. 1. The process 600 may include different or additional steps than those described in conjunction with FIG. 6 in some embodiments or perform steps in different orders than the order described in conjunction with FIG. 6.

In one embodiment, the image processing engine 320 receives 610 a set of images of an optical property modifying device 120 for a nucleic acid disease diagnostic test captured by an optical sensor of a mobile device 110. The image processing engine 320 determines 620, for each image in the set, whether the surface of the optical property modifying device 120 is shown in the image. The image processing engine 320 selects 630 one or more images of the set that are determined to show the surface. The image analysis engine 325 determines 640 a test result for the nucleic acid disease diagnostic test based on the one or more images. The diagnostic test engine 330 provides 650 the test result for display on the mobile device 110.

VI. Alternative Embodiments

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

What is claimed is:

1. A method for determining results for image-based diagnostic tests, the method comprising:
receiving one or more images of an optical property modifying device for a diagnostic test captured by an optical sensor of a mobile device, the optical property modifying device comprising a plurality of reaction chambers configured to perform a reaction between a biological sample and at least an optical property modifying reagent, wherein a surface of the optical property modifying device comprises an electronic display;

determining that the electronic display of the optical property modifying device is shown in the one or more images;

determining that an image of the set of one or more images shows a known geometric characteristic associated with the optical property modifying device;

determining one or more test results for the diagnostic test based at least in part on the image; and providing the one or more test results for presentation by the mobile device.

2. The method of claim 1, wherein the electronic display is a liquid crystal display.

3. The method of claim 1, wherein the electronic display is an organic light emitting diode display.

4. The method of claim 1, wherein the electronic display is an electronic paper display.

5. The method of claim 1, wherein the electronic display comprises one or more light emitting diodes.

6. The method of claim 1, further comprising providing a notification relating to the one or more test results on the mobile device via audio signals or tactile signals.

7. The method of claim 1, wherein the reaction is a nucleic acid amplification assay, an immunoassay or enzyme-linked immunosorbent assays (ELISAs) that changes the properties of a solution that comprises the biological sample and the optical property modifying reagent in the reaction chambers.

8. The method of claim 1, further comprising providing the one or more test results, a geographical location of the mobile device, and a timestamp of the geographical location to a computer server.

9. The method of claim 1, further comprising generating a message comprising sponsored content based on the one or more test results and providing the message to the mobile device.

10. The method of claim 1, further comprising providing information associated with the one or more test results to a pharmacy or healthcare provider.

11. The method of claim 1, further comprising providing information obtained from the group consisting of: a Global Positioning System (GPS) sensor, a motion sensor, a proximity sensor, or a temperature sensor, on a mobile device.

12. The method of claim 1, wherein a surface of the optical property modifying device comprises a machine-readable symbol that can be scanned to provide the mobile device or the user with information for the diagnostic test.

13. The method of claim 12, wherein the machine-readable symbol is a QR code.

14. The method of claim 12, wherein the machine-readable symbol is a bar code.

15. The method of claim 1, further comprising determining that an image of the one or more images shows a known color characteristic associated with the optical property modifying device.

16. The method of claim 1, further comprising determining the one or more test results in parallel or in series based at least in part on the image.

17. A computer program product comprising a non-transitory computer readable storage medium having instructions encoded thereon that, when executed by a processor, cause the processor to:

receive one or more images of an optical property modifying device for a diagnostic test captured by an optical sensor of a mobile device, the optical property modifying device comprising a plurality of reaction chambers configured to perform a reaction between a biological sample and at least an optical property modifying reagent, wherein a surface of the optical property modifying device comprises an electronic display;

determine that the electronic display of the optical property modifying device is shown in the one or more images;

determine that an image of the one or more images shows a known geometric characteristic associated with the optical property modifying device;

determine one or more test results for the diagnostic test based at least in part on the image; and provide the one or more test results for presentation by the mobile device.

18. The computer program product of claim 17, wherein the non-transitory computer readable storage medium further comprises instructions that when executed by the processor cause the processor to:

provide one or more notifications relating to the one or more test results on the mobile device via audio signals or tactile signals.

19. The computer program product of claim 17, wherein the electronic display comprises one or more light emitting diodes.

* * * * *

UNITED STATES PATENT AND TRADEMARK OFFICE
CERTIFICATE OF CORRECTION

PATENT NO. : 11,080,848 B2
APPLICATION NO. : 16/155829
DATED : August 3, 2021
INVENTOR(S) : Ivan Krastev Dimov et al.

It is certified that error appears in the above-identified patent and that said Letters Patent is hereby corrected as shown below:

In the Claims

In Column 17, Claim 1, Line 4, delete "of the set of" and insert -- of the --, therefor.

Signed and Sealed this
Ninth Day of November, 2021

Drew Hirshfeld
*Performing the Functions and Duties of the
Under Secretary of Commerce for Intellectual Property and
Director of the United States Patent and Trademark Office*